US011757233B2

(12) United States Patent
Kokovidis et al.

(10) Patent No.: US 11,757,233 B2
(45) Date of Patent: Sep. 12, 2023

(54) CABLE DETECTION USING LIGHT SENSOR (71) Applicant: Draeger Medical Systems, Inc., Andover, MA (US)

(72) Inventors: Georgios Kokovidis, Waltham, MA (US); Peter A. Lund, Nashua, NH (US)

(73) Assignee: Drägerwerk AG & Co. KGaA, Lübeck (DE)

( * ) Notice: Subject to any disclaimer, the term of this patent is extended or adjusted under 35 U.S.C. 154(b) by 83 days.

(21) Appl. No.: 17/461,562

(22) Filed: Aug. 30, 2021

(65) Prior Publication Data
US 2022/0140532 A1    May 5, 2022

Related U.S. Application Data

(60) Provisional application No. 63/109,597, filed on Nov. 4, 2020.

(51) Int. Cl.
*H01R 13/641* (2006.01)
*H01R 13/66* (2006.01)
*A61B 5/273* (2021.01)
*A61B 5/318* (2021.01)
*H01R 13/717* (2006.01)

(52) U.S. Cl.
CPC .......... *H01R 13/641* (2013.01); *A61B 5/273* (2021.01); *H01R 13/6683* (2013.01); *A61B 5/318* (2021.01); *H01R 13/7175* (2013.01); *H01R 2201/12* (2013.01)

(58) Field of Classification Search
CPC .............. H01R 13/641; H01R 13/6683; H01R 13/7175; H01R 2201/12; A61B 5/273; A61B 5/318
See application file for complete search history.

(56) References Cited

U.S. PATENT DOCUMENTS

| | | | | |
|---|---|---|---|---|
| 5,550,755 A | * | 8/1996 | Martin | H04H 60/04 348/E5.022 |
| 6,707,172 B2 | * | 3/2004 | Tronolone | H01R 13/641 307/134 |
| 7,814,240 B2 | * | 10/2010 | Salgado | H01R 13/7035 710/16 |
| 8,360,801 B2 | * | 1/2013 | Lynch | H01R 13/641 439/488 |
| 8,626,961 B2 | * | 1/2014 | Stenmark | H04M 1/72412 710/15 |

FOREIGN PATENT DOCUMENTS

| | | | | | |
|---|---|---|---|---|---|
| GB | 2540972 A | * | 2/2017 | ........... | G01R 31/045 |
| GB | 2540973 A | * | 2/2017 | ........... | G01R 31/045 |

* cited by examiner

*Primary Examiner* — Tho D Ta (74) *Attorney, Agent, or Firm* — Nolte Lackenbach Siegel (57) ABSTRACT

A connector detection system includes a connector interface including a connector port having an interior volume configured receive a connector of a cable; and an optical sensor. The optical sensor includes a transmitter configured to transmit a light beam across the interior volume; a receiver configured to monitor for a reflected light beam corresponding to the transmitted light beam; and processing circuitry configured to determine whether the connector is inserted into the interior volume based on a monitoring for the reflected light beam.

20 Claims, 6 Drawing Sheets

CABLE DETECTION USING LIGHT SENSOR

CROSS-REFERENCE TO RELATED APPLICATIONS

This application claims the priority of prior provisional U.S. Patent Application No. 63/109,597 filed on Nov. 4, 2020, the contents of which being incorporated herein by reference in its entirety.

BACKGROUND

Patient monitors are devices that are configured to monitor a patient's physiological data, receive physiological data from another device, and either display a patient's physiological data, output a patient's physiological data, or both. A patient monitoring device may be configured to be worn by a patient, may be a hand-held device, may be docked to or undocked from a larger unit such as a monitor mount, and, thus, may be transportable. For example, a monitor mount may be a larger patient monitor or a console that has a docking interface or docking receptacle to which the patient monitor can be removably docked.

A patient monitor may be implemented to monitor cardiac signals from a patient via electrocardiogram (ECG) sensors connected to an ECG lead set. Commonly used ECG lead set configurations include three-lead, five-lead, six-lead and 12-lead configurations. In a 12-lead ECG configuration, for example, ten electrodes (i.e., sensors) are placed on predetermined locations of the skin of the patient body. The overall magnitude of the heart's electrical potential is then measured from twelve different angles ("leads") and is recorded over a period of time (e.g., 10 seconds). In this way, the overall magnitude and direction of the heart's electrical activity is captured throughout the heartbeat. The ECG lead set may further include a processor that is embedded therein. The processor may be an electrically erasable programmable read-only memory (EEPROM), a central processing unit (CPU), a digital signal processor (DSP), a general-purpose microprocessor, an application specific integrated circuit (ASIC), a field programmable logic array (FPGA), or other equivalent integrated or discrete logic circuitry. For example, the processor may be embedded in a connector of the ECG lead set. The processor is configured to store data relevant to the ECG lead set and the patient monitor is capable of carrying out both read and write operations with respect to the stored data (e.g., EEPROM data).

ECG lead sets with an embedded processor may be automatically detectable by the patient monitor. In contrast, ECG lead sets without an embedded processor are not automatically detectable. Thus, a patient monitor that is capable of automatically detecting both types of cables may be desirable.

SUMMARY

One or more embodiments provide a connector detection system, including: a connector interface comprising a connector port having an interior volume configured receive a connector of a cable; and an optical sensor. The optical sensor may include a transmitter configured to transmit a light beam across the interior volume, a receiver configured to monitor for a reflected light beam corresponding to the transmitted light beam, and processing circuitry configured to determine whether the connector is inserted into the interior volume based on a monitoring for the reflected light beam.

One or more embodiments may provide a physiological patient monitoring device, including: frontend circuitry configured to receive and process physiological measurements received from a cable connected to a person; a connector interface comprising a connector port having an interior volume configured receive a connector of the cable; an optical sensor; and a system controller. The optical sensor may include a transmitter configured to transmit a light beam across the interior volume; a receiver configured to monitor for a reflected light beam corresponding to the transmitted light beam; and processing circuitry configured to determine whether a connector is inserted into the interior volume based on a monitoring for the reflected light beam. The system controller may be configured to activate the frontend circuitry in response to the processing circuitry determining that the connector is inserted into the interior volume and deactivate the frontend circuitry in response to the processing circuitry determining that the connector is not inserted into the interior volume.

One or more embodiments may provide a method of detecting a connector of a cable inserted into a connector port having an interior volume configured receive the connector. The method may include transmitting a light beam across the interior volume, monitoring for a reflected light beam corresponding to the transmitted light beam, and determining whether the connector is inserted into the interior volume based on a monitoring for the reflected light beam.

BRIEF DESCRIPTION OF THE DRAWINGS

In the drawings, like reference numbers generally indicate identical, functionally similar, and/or structurally similar elements.

DETAILED DESCRIPTION

In the following, details are set forth to provide a more thorough explanation of the embodiments. However, it will be apparent to those skilled in the art that embodiments may be practiced without these specific details. In other instances, well-known structures and devices are shown in block diagram form or in a schematic view rather than in detail in order to avoid obscuring the embodiments. In addition, features of the different embodiments described hereinafter may be combined with each other, unless specifically noted otherwise. For example, variations or modifications described with respect to one of the embodiments may also be applicable to other embodiments unless noted to the contrary.

Further, equivalent or like elements or elements with equivalent or like functionality are denoted in the following description with equivalent or like reference numerals. As the same or functionally equivalent elements are given the same reference numbers in the figures, a repeated description for elements provided with the same reference numbers may be omitted. Hence, descriptions provided for elements having the same or like reference numbers are mutually exchangeable.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

In the present disclosure, expressions including ordinal numbers, such as "first", "second", and/or the like, may modify various elements. However, such elements are not limited by the above expressions. For example, the above expressions do not limit the sequence and/or importance of the elements. The above expressions are used merely for the purpose of distinguishing an element from the other elements. For example, a first box and a second box indicate different boxes, although both are boxes. For further example, a first element could be termed a second element, and similarly, a second element could also be termed a first element without departing from the scope of the present disclosure.

Directional terminology, such as "top", "bottom", "below", "above", "front", "behind", "back", "leading", "trailing", etc., may be used with reference to the orientation of the figures being described. Because parts of embodiments can be positioned in a number of different orientations, the directional terminology is used for purposes of illustration. It is to be understood that other embodiments may be utilized and structural or logical changes may be made without departing from the scope defined by the claims. The following detailed description, therefore, is not to be taken in a limiting sense. Directional terminology used in the claims may aid in defining one element's spatial or positional relation to another element or feature, without being limited to a specific orientation.

Instructions may be executed by one or more processors, such as one or more central processing units (CPU), digital signal processors (DSPs), general purpose microprocessors, application specific integrated circuits (ASICs), field programmable logic arrays (FPGAs), or other equivalent integrated or discrete logic circuitry. Accordingly, the term "processor," as used herein refers to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements. A "controller," including one or more processors, may use electrical signals and digital algorithms to perform its receptive, analytic, and control functions, which may further include corrective functions. Thus, a controller is a specific type of processing circuitry, comprising one or more processors and memory, that implements control functions by way of generating control signals.

A sensor refers to a component which converts a physical quantity to be measured to an electric signal, for example, a current signal or a voltage signal. The physical quantity may for example comprise electromagnetic radiation (e.g., photons of infrared or visible light), a magnetic field, an electric field, a pressure, a force, a temperature, a current, or a voltage, but is not limited thereto.

Signal conditioning, as used herein, refers to manipulating an analog signal in such a way that the signal meets the requirements of a next stage for further processing. Signal conditioning may include converting from analog to digital (e.g., via an analog-to-digital converter), amplification, filtering, converting, biasing, range matching, isolation and any other processes required to make a sensor output suitable for processing after conditioning.

Backwards compatibility is the ability of a newer system or device to be able to communicate and/or interface with older, so-called "legacy" components, software, or systems. An advantage of backward compatibility is that some components of a system (e.g., the patient monitor) can be upgraded to a newer version or model, while still retaining the ability to communicate older accessories that may be implementing interface connectors, software, or hardware. Consequently, users are able to upgrade their system "piecemeal" and/or they can choose to upgrade more critical components while still retaining usability of legacy components.

As defined herein, a "smart" cable is a cable that comprises an embedded processor that is configured to operate to some extent interactively and autonomously with another device. The processor may be an electrically erasable programmable read-only memory (EEPROM), a central processing unit (CPU), a digital signal processor (DSP), a general-purpose microprocessor, an application specific integrated circuit (ASIC), a field programmable logic array (FPGA), or other equivalent integrated or discrete logic circuitry. In contrast, a "legacy" cable is a cable that does not comprise an embedded processor that is configured to operate to some extent interactively and autonomously with another device.

Smart cables include smart ECG lead sets and legacy cables include legacy ECG lead sets. In addition to enabling the transfer of data between the patient monitor and the smart ECG lead set, a smart ECG lead set also has an advantage over legacy lead sets in that the smart lead set is automatically detectable by the patient monitor. In other words, the patient monitor can automatically detect that a smart lead set has been connected. In contrast, a conventional patient monitor is not able to detect the presence of a legacy lead set or any other legacy cable or legacy connector. In this case, a user must navigate a series of menus items on a graphical user interface or other user input to indicate to the patient monitor both that a cable has been connected and the type of cable. The process of connecting legacy lead sets and cables is cumbersome and impedes workflow.

Figure 1:
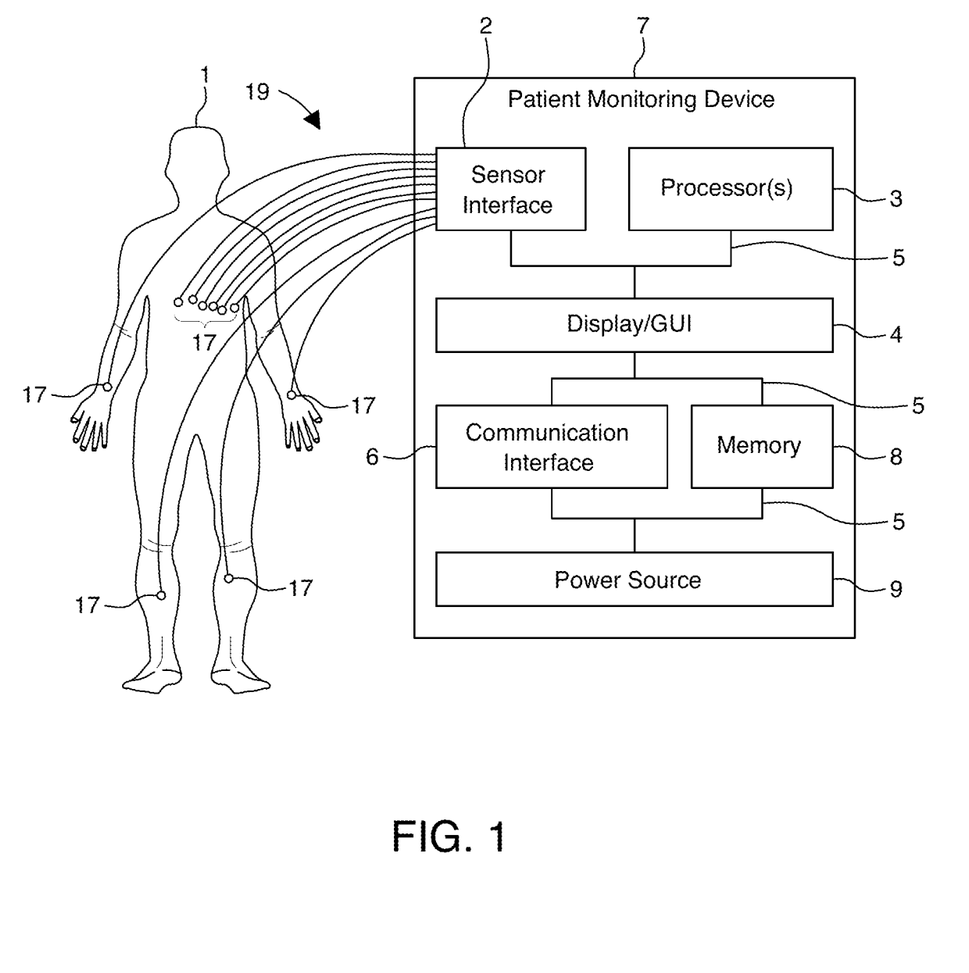
FIG. 1 shows a physiological monitoring system according to one or more embodiments.

FIG. 1 shows a physiological monitoring system according to one or more embodiments. As shown in FIG. 1, the system includes a patient monitoring device 7 (i.e., a physiological monitoring device) capable of receiving physiological data from various sensors 17 connected to a patient 1.

In general, it is contemplated by the present disclosure that the patient monitoring device 7 includes electronic components and/or electronic computing devices operable to receive, transmit, process, store, and/or manage patient data and information associated performing the functions of the system, which encompasses any suitable processing device adapted to perform computing tasks consistent with the execution of computer-readable instructions stored in a memory or a computer-readable recording medium.

Further, any, all, or some of the computing devices in the patient monitoring device 7 may be adapted to execute any operating system, including Linux, UNIX, Windows Server, etc., as well as virtual machines adapted to virtualize execution of a particular operating system, including customized and proprietary operating systems. The patient monitoring device 7 is further equipped with components to facilitate communication with other computing devices over one or more network connections, which may include connections to local and wide area networks, wireless and wired networks, public and private networks, and any other communication network enabling communication in the system.

As shown in FIG. 1, the patient monitoring device 7 may be, for example, a patient monitor implemented to monitor various physiological parameters of the patient 1 via the sensors 17. The patient monitoring device 7 may include a sensor interface 2, one or more processors 3, a display/graphical user interface (GUI) 4, a communication interface 6, a memory 8, and a power source 9. The sensor interface 2 may be implemented in hardware or combination of hardware and software and is used to connect via wired and/or wireless connections 19 to one or more sensors 17 for gathering physiological data from the patient 1. The sensors 17 may be physiological sensors and/or medical devices configured to measure one or more of the physiological parameters and output the measurements via a corresponding one or more connections 19 to the sensor interface 2. Thus, the connections 19 represent one or more wired or wireless communication channels configured to at least transmit sensor data from a corresponding sensor 17 to the sensor interface 2.

By way of example, the sensors 17 may include electrodes that attach to the patient 1 for reading electrical signals generated by or passed through the patient 1. The sensors 17 may be configured to measure vital signs, measure electrical stimulation, measure brain electrical activity such as in the case of a electroencephalogram (EEG), measure blood oxygen saturation fraction from absorption of light at different wavelengths as it passes through a finger, measure a carbon dioxide (CO2) level and/or other gas levels in an exhalation stream using infrared spectroscopy, measure oxygen saturation on the surface of the brain or other regions, measure cardiac output from invasive blood pressure and temperature measurements, measure induced electrical potentials over the cortex of the brain, measure blood oxygen saturation from an optical sensor coupled by fiber to the tip of a catheter, and/or measure blood characteristics using absorption of light.

The data signals from the sensors 17 may include, for example, sensor data related to an electrocardiogram (ECG), non-invasive peripheral oxygen saturation (SpO2), non-invasive blood pressure (NIBP), body temperature, end tidal carbon dioxide (etCO2), apnea detection, and/or other physiological data, including those described herein. The one or more processors 3 may be used for controlling the general operations of the patient monitoring device 7, as well as processing sensor data received by the sensor interface 2. Each one of the one or more processors 3 may be, but are not limited to, a central processing unit (CPU), a hardware microprocessor, a multi-core processor, a single core processor, a field programmable gate array (FPGA), a microcontroller, an application specific integrated circuit (ASIC), a digital signal processor (DSP), or other similar processing device capable of executing any type of instructions, algorithms, or software for controlling the operation and performing the functions of the patient monitoring device 7.

The display/GUI 4 may be configured to display various patient data, sensor data, and hospital or patient care information, and includes a user interface implemented for allowing interaction and communication between a user and the patient monitoring device 7. The display/GUI 4 may include a keyboard, as well as a display, such as a liquid crystal display (LCD), cathode ray tube (CRT) display, thin film transistor (TFT) display, light-emitting diode (LED) display, high definition (HD) display, or other similar display device that may include touch screen capabilities. The display/GUI 4 may provide a means for inputting instructions or information directly to the patient monitoring device 7. The patient information displayed may, for example, relate to the measured physiological parameters of the patient 1 (e.g., blood pressure, heart related information, pulse oximetry, respiration information, etc.) as well as information related to the transporting of the patient 1 (e.g., transport indicators).

The communication interface 6 may enable the patient monitoring device 7 to directly or indirectly (via, for example, a monitor mount) communicate with one or more computing networks and devices, including one or more sensors 17, workstations, consoles, computers, monitoring equipment, alert systems, and/or mobile devices (e.g., a mobile phone, tablet, or other hand-held display device). The communication interface 6 may include various network cards, interfaces, communication channels, cloud, antennas, and/or circuitry to enable wired and wireless communications with such computing networks and devices. The communication interface 6 may be used to implement, for example, a Bluetooth connection, a cellular network connection, and/or a Wi-Fi connection with such computing networks and devices. Example wireless communication connections implemented using the communication interface 6 include wireless connections that operate in accordance with, but are not limited to, IEEE802.11 protocol, a Radio Frequency For Consumer Electronics (RF4CE) protocol, and/or IEEE802.15.4 protocol (e.g., ZigBee protocol). In essence, any wireless communication protocol may be used.

Additionally, the communication interface 6 may enable direct (i.e., device-to-device) communications (e.g., messaging, signal exchange, etc.) such as from a monitor mount to the patient monitoring device 7 using, for example, a universal serial bus (USB) connection or other communication protocol interface. The communication interface 6 may also enable direct device-to-device connection to other devices such as to a tablet, computer, or similar electronic device; or to an external storage device or memory.

The memory 8 may be a single memory device or one or more memory devices at one or more memory locations that may include, without limitation, one or more of a random-access memory (RAM), a memory buffer, a hard drive, a database, an erasable programmable read only memory (EPROM), an electrically erasable programmable read only memory (EEPROM), a read only memory (ROM), a flash memory, hard disk, various layers of memory hierarchy, or any other non-transitory computer readable medium. The memory 8 may be used to store any type of instructions and patient data associated with algorithms, processes, or operations for controlling the general functions and operations of the patient monitoring device 7.

The power source 9 may include a self-contained power source such as a battery pack and/or include an interface to be powered through an electrical outlet (either directly or by way of a monitor mount). The power source 9 may also be a rechargeable battery that can be detached allowing for replacement. In the case of a rechargeable battery, a small built-in back-up battery (or super capacitor) can be provided for continuous power to be provided to the patient monitoring device 7 during battery replacement. Communication between the components of the patient monitoring device 7 (e.g., components 2, 3, 4, 6, 8, and 9) may be established using an internal bus 5.

Accordingly, the patient monitoring device 7 is attached to one or more of several different types of sensors 17 and may be configured to measure and readout physiological data related to the patient 1 (e.g., as shown on the left side of FIG. 1). One or more sensors 17 may be attached to patient monitoring device 7 by, for example, a wired connection coupled to the sensor interface 2. Additionally, or alternatively, one or more sensors 17 may be a wireless sensor that is communicatively coupled to the patient monitoring device 7 via the communication interface 6, which includes circuitry for receiving data from and sending data to one or more devices using, for example, a Wi-Fi connection, a cellular network connection, and/or a Bluetooth connection.

The data signals from the sensors 17 received by the patient monitoring device 7 may include sensor data related to, for example, body temperature (BT), pulse (heart rate (HR)), and breathing rate (respiratory rate) (RR), an ECG, SpO2, NIBP, and/or etCO2.

The data signals received from the sensors, including an ECG sensor and an SpO2 sensor, may be analog signals. For example, the data signals for the ECG and the SpO2 are input to the sensor interface 2, which can include an ECG data acquisition circuit and an SpO2 data acquisition circuit. Both the ECG data acquisition circuit and the SpO2 data acquisition circuit may include amplifying and filtering circuity as well as analog-to-digital (A/D) circuity that converts the analog signal to a digital signal using amplification, filtering, and A/D conversion methods. In the event that the ECG sensor and the SpO2 sensor are wireless sensors, the sensor interface 2 may receive the data signals from a wireless commination module. Thus, a sensor interface is a component which may be configured to interface with one or more sensors 17 and receive sensor data therefrom.

In other examples, the data signals related to NIBP, body temperature, and etCO2 may be received from sensors 17 to the sensor interface 2, which may include a physiological parameter interface such as serial interface circuitry for receiving and processing the data signals related to NIBP, temperature, and etCO2. In FIG. 1, the ECG data acquisition circuit, an SpO2 data acquisition circuit, and physiological parameter interface are described as part of the sensor interface 2 and are not separately shown. However, it is contemplated by the present disclosure that the ECG data acquisition circuit, the SpO2 data acquisition circuit, and physiological parameter interface may be implemented as circuits separate from the sensor interface 2. In the event that the NIBP sensor, the temperature sensor, and the etCO2 sensor are wireless sensors, the sensor interface 2 may receive the data signals from a wireless commination module.

The processing performed by the ECG data acquisition circuit, the SpO2 data acquisition circuit, and an external physiological parameter interface (also not separately shown) may generate analog data waveforms or digital data waveforms that are analyzed by a microcontroller. The microcontroller may be one of the processors 3. The microcontroller, for example, analyzes the digital waveforms to identify certain digital waveform characteristics and threshold levels indicative of conditions (abnormal and normal) of the patient 1 using one or more monitoring methods. A monitoring method may include comparing an analog or a digital waveform characteristic or an analog or digital value to one or more threshold values and generating a comparison result based thereon. The microcontroller may be, for example, a processor, an FPGA, an ASIC, a DSP, a microcontroller, or similar processing device. The microcontroller may include a memory or uses a separate memory 8. The memory may be, for example, a RAM, a memory buffer, a hard drive, a database, an EPROM, an EEPROM, a ROM, a flash memory, a hard disk, or any other non-transitory computer readable medium.

The memory may store software or algorithms with executable instructions and the microcontroller may execute a set of instructions of the software or algorithms in association with executing different operations and functions of the patient monitoring device 7 such as analyzing the digital data waveforms related to the data signals from the sensors 17.

Figure 2:
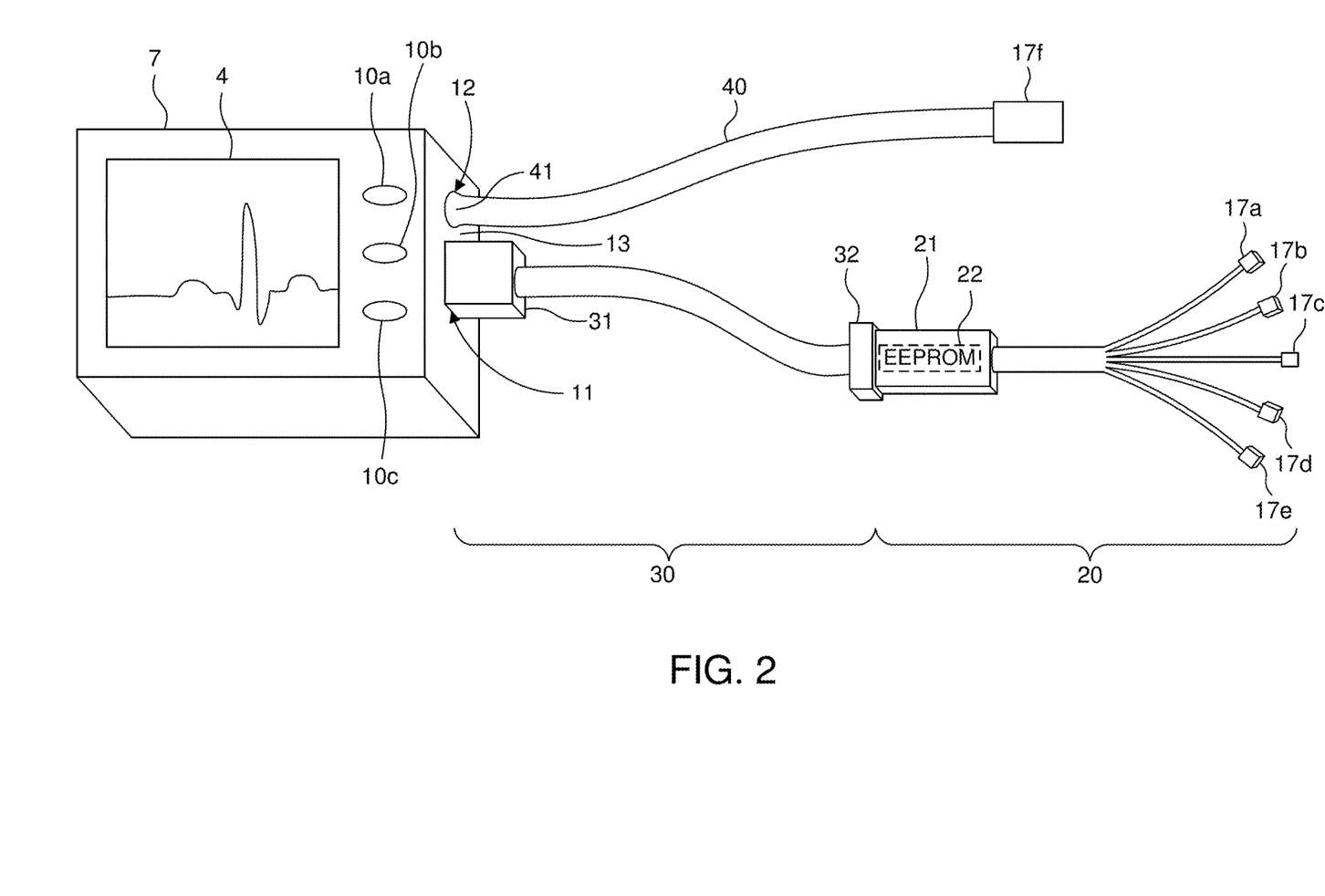
FIG. 2 shows a physiological monitoring system according to one or more embodiments.

FIG. 2 shows a physiological monitoring system according to one or more embodiments. The patient monitoring device 7 has at least ECG monitoring and NIBP monitoring functionalities. However, it will be appreciated that the patient monitoring device 7 may monitor other types of physiological parameters as well via other cables and ports that are not shown, as described in conjunction with FIG. 1.

The patient monitoring device 7 may include the display 4 and user input buttons 10a, 10b, and 10c for receiving user input. The display 4 may display a GUI, including menu icons and prompts. A user may manipulate the user input buttons 10a, 10b, and 10b to navigate the menu icons and prompts for providing user input. Additionally, or alternatively, the display 4 may have touch-screen capabilities that enables a user to provide user input by interacting with menu icons and prompts displayed on the display 4 via touch.

The patient monitoring device 7 may further include an ECG cable interface 11, such as a connector port, arranged at a connector housing 13 of the patient monitoring device 7. The ECG cable interface 11 may be configured to receive a cable and electrically connect a cable to the patient monitoring device 7. The ECG cable interface 11 may be a slot or recess whose volume is defined by a number of sidewalls. Thus, the cable interface 11 may further include a number of pins for engaging with pin holes of the cable or a number of pin holes for engaging with pins of the cable, depending on the configuration. Any cable interface may be used, including any male-to-female connector interface or female-to-male connector interface. The patient monitoring device 7 may be configured to receive physiological data, in this case ECG data, from the cable connected at the ECG cable interface 11, process the physiological data, and display processed physiological data onto the display 4.

A cable system may include an ECG lead set 20 and may include an optional ECG extension cable 30. The cable system represents the one or more of the connections 19 shown in FIG. 1. In this case, the ECG lead set 20 includes five leads with each lead terminating at a sensor (e.g., an electrode) 17a-17e that is attached to the patient for measuring ECG data. It is noted that in practice, the ECG lead set 20 can include any number of leads. At the opposite end, the ECG lead set 20 may have a connector 21. The connector 21 may be configured to be connected directly or indirectly to the patient monitoring device 7. The connector 21 may also be configured to be connected the optional ECG extension cable 30. The ECG extension cable 30 is used, for example, when the ECG lead set 20 is not long enough to fully extend from the patient to the patient monitoring device 7. Thus, the connector 21 may be an interface that is configured to be electrically coupled to the patient monitoring device 7 and to the ECG extension cable 30. Any connector interface may be used for the connector 21, including any male-to-female connector interface or female-to-male connector interface.

The ECG lead set 20 may be a "smart" cable in that it comprises an electrically erasable programmable read-only memory (EEPROM) 22 that is embedded therein and provides additional functionality compared to non-smart cables (as detailed hereinbelow). For example, the EEPROM 22 is configured to operate to some extent interactively and autonomously with the patient monitoring device 7. Alternatively, the ECG lead set 20 may be a "legacy" cable that does not contain an EEPROM. Thus, the EEPROM 22 is shown as being optional, as indicated by the dotted outline.

When the EEPROM 22 is present, it may be embedded in the connector 21 of the ECG lead set 20. The EEPROM may be configured to store data relevant to the ECG lead set and the patient monitoring device 7 is capable of carrying out both read and write operations with respect to the EEPROM data.

In addition to enabling the transfer of EEPROM data between the patient monitor and the smart lead set, a smart lead set also has an advantage over legacy lead sets in that the smart lead set is automatically detectable by the patient monitoring device 7. In other words, the patient monitoring device 7 may automatically detect that a smart lead set has been connected. In contrast, a conventional patient monitor may not be able to detect the presence of a legacy lead set or any other cable or connector that does not have a "smart" feature like an EEPROM.

A smart cable, such as a smart ECG lead set or a smart ECG extension cable may include a circuit (e.g., a semiconductor chip) that is automatically activated when it detects that it has been plugged in. The circuit may use the EEPROM 22 to automatically identify itself to the patient monitoring device 7, which may include transmitting authentication information, lead information (e.g., indicting a number of leads), and whether it is an extension cable or a lead set. The patient monitoring device 7 automatically detects the smart cable when electrical contact is made and activates its ECG frontend circuitry to enable the patient monitoring device 7 to read and process ECG measurements.

The EEPROM 22 may be configured to store data relevant to the ECG lead set 20, including information such as a number of leads, authentication information, number of use information, and so forth.

The number of leads of various types of ECG lead sets can vary. For example, existing ECG lead sets have anywhere between three wires and 12 wires (which results in 3 to 12 lead views, depending on the number of wires used). However, any number of leads is possible. The patient monitoring device 7 may process information on as many leads as are present in the ECG front end. This processing allows for proper processing and display of ECG data by the patient monitoring device 7. For example, the ECG cable may implement an EEPROM (or other processor) to enable the monitor to communicate with, and read information from, the EEPROM. On the other hand, when a legacy ECG cable (e.g., without an EEPROM) is used, the patient monitoring device 7 may not automatically obtain information regarding the number of leads. In this scenario, a clinical provider may need to manually put in such information via GUI.

Reading the EEPROM 22 is also critical for detecting whether an ECG lead set is correctly plugged into the patient monitoring device 7. The EEPROM 22 may store authentication information that allows the patient monitoring device 7 to verify that the ECG lead set is authentic and not a counterfeit. Counterfeit leads may have poor quality control (or none at all), which could endanger patients if, for example, the leads are generating inaccurate information because medical personnel rely on the signals acquired by the leads in order to make treatment decisions. Furthermore, counterfeit leads could be defective and injure the patient.

The EEPROM 22 may store usage information indicating its number of uses and provide the number of uses to the patient monitoring device 7 so that the patient monitoring device 7 may determine whether the ECG lead set has exceeded its lifetime number of uses. For example, some ECG lead sets are manufactured for a one-time use and may not have been designed or manufactured to be repeatedly sanitized and reused. For another example, a one-time use ECG lead may experience degradation of materials over time from repeated exposure to chemicals, to which the ECG leads may not be intended to be exposed. Alternatively, the one-time use ECG leads may have hard-to-clean surface or components in which bacteria or other germs could grow and affect subsequent patients upon repeated use. The ECG lead set 20 may keep track of its number of uses by incrementing a counter and storing the number of uses in the EEPROM 22. Alternatively, the patient monitoring device 7 may track the number of uses and write the number of uses into the EEPROM 22. Thus, the patient monitoring device 7 may be capable of carrying out both read and write operations with respect to the EEPROM data. The EEPROM 22 may also store information that identifies the cable as a cable with electrosurgical unit (ESU) protection or without ESU protection.

The ECG extension cable 30 may include a first connector 31 at a first end that is configured to engage with the cable interface 11 of the patient monitoring device 7 and a second connector 32 at a second end that is configured to engage with the connector 21 of the patient monitoring device 7. Both connectors 31 and 32 may be connectors arranged at the terminal ends of the extension cable 30 for the transmission of electrical signals between the ECG lead set 20 and the patient monitoring device 7.

The patient monitoring device 7 may further include an NIBP cable interface 12, such as a connector port, arranged at the connector housing 13 of the patient monitoring device 7. The NIBP cable interface 12 is configured to receive a cable and electrically connect an NIBP cable 40 to the patient monitoring device 7. The NIBP cable interface 12 may be a slot or recess whose volume is defined by a number of sidewalls. Thus, NIBP cable interface 12 may further include a number of pins for engaging with pin holes of the cable or a number of pin holes for engaging with pins of the cable, depending on the configuration. Any cable interface may be used, including any male-to-female connector interface or female-to-male connector interface. The patient monitoring device 7 may be configured to receive physiological data, in this case NIBP data, from the cable connected at the NIBP cable interface 12, process the physiological data, and display processed physiological data onto the display 4.

The NIBP cable 40 may include an NIBP sensor 17f at one end that is attached to the patient for taking NIBP measurements. At the opposite end, the NIBP cable 40 may include a connector 41 that is configured to be received by the NIBP cable interface 12 and electrically connected to the patient monitoring device 7 for providing NIBP measurements thereto.

Figure 3A:
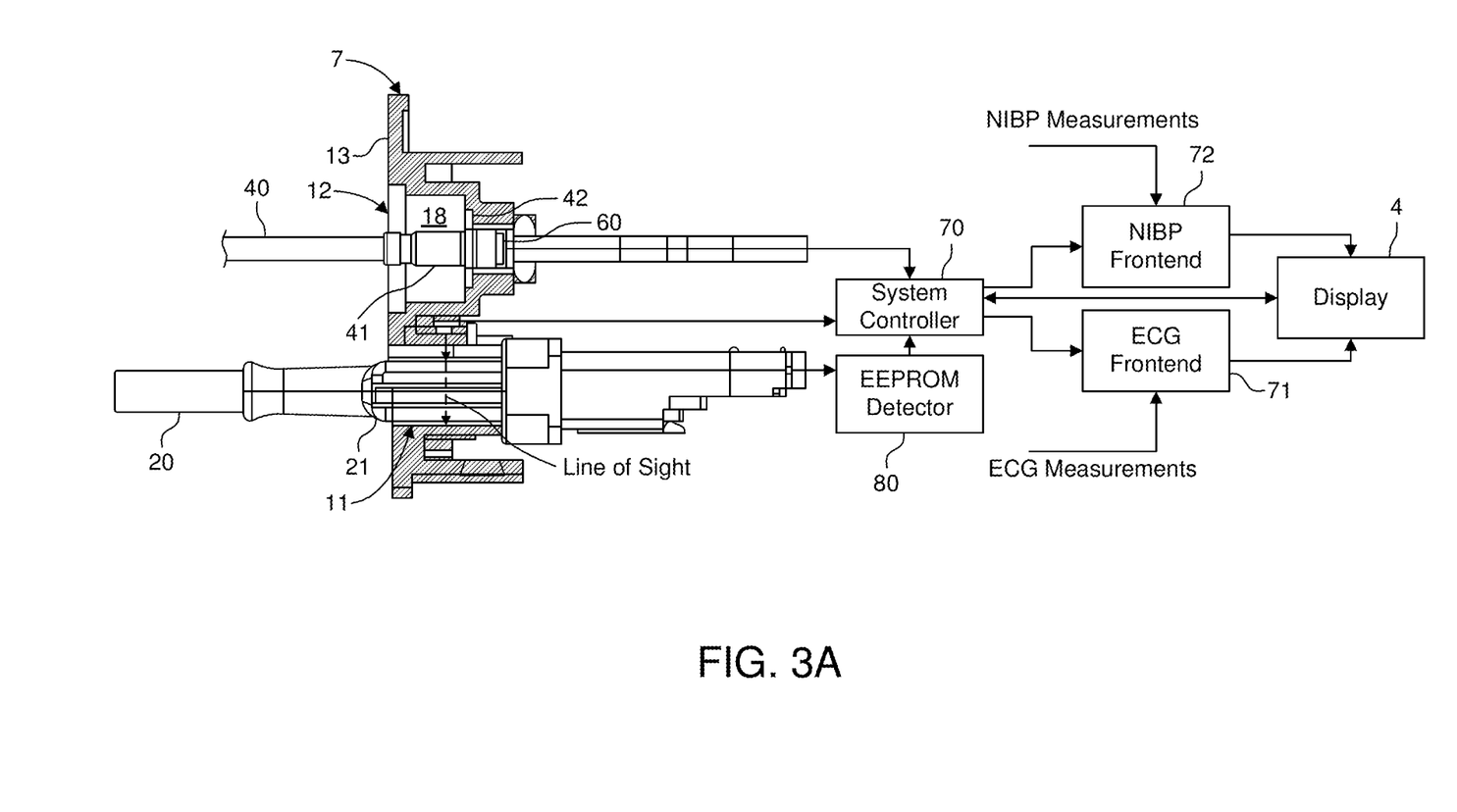
FIGS. 3A-3C illustrate a connector detection system according to one or more embodiments.
Figure 3B:
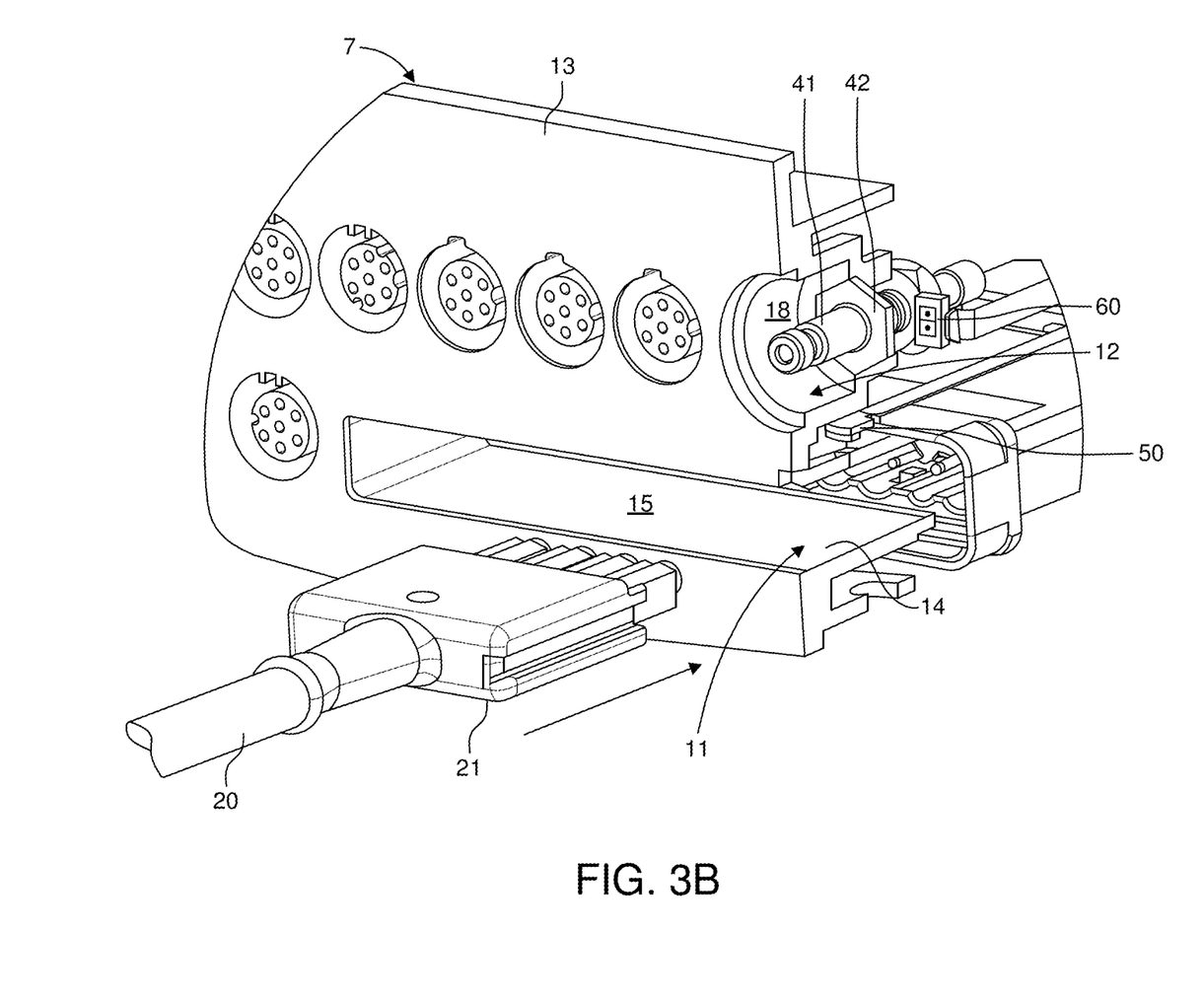
Figure 3C:
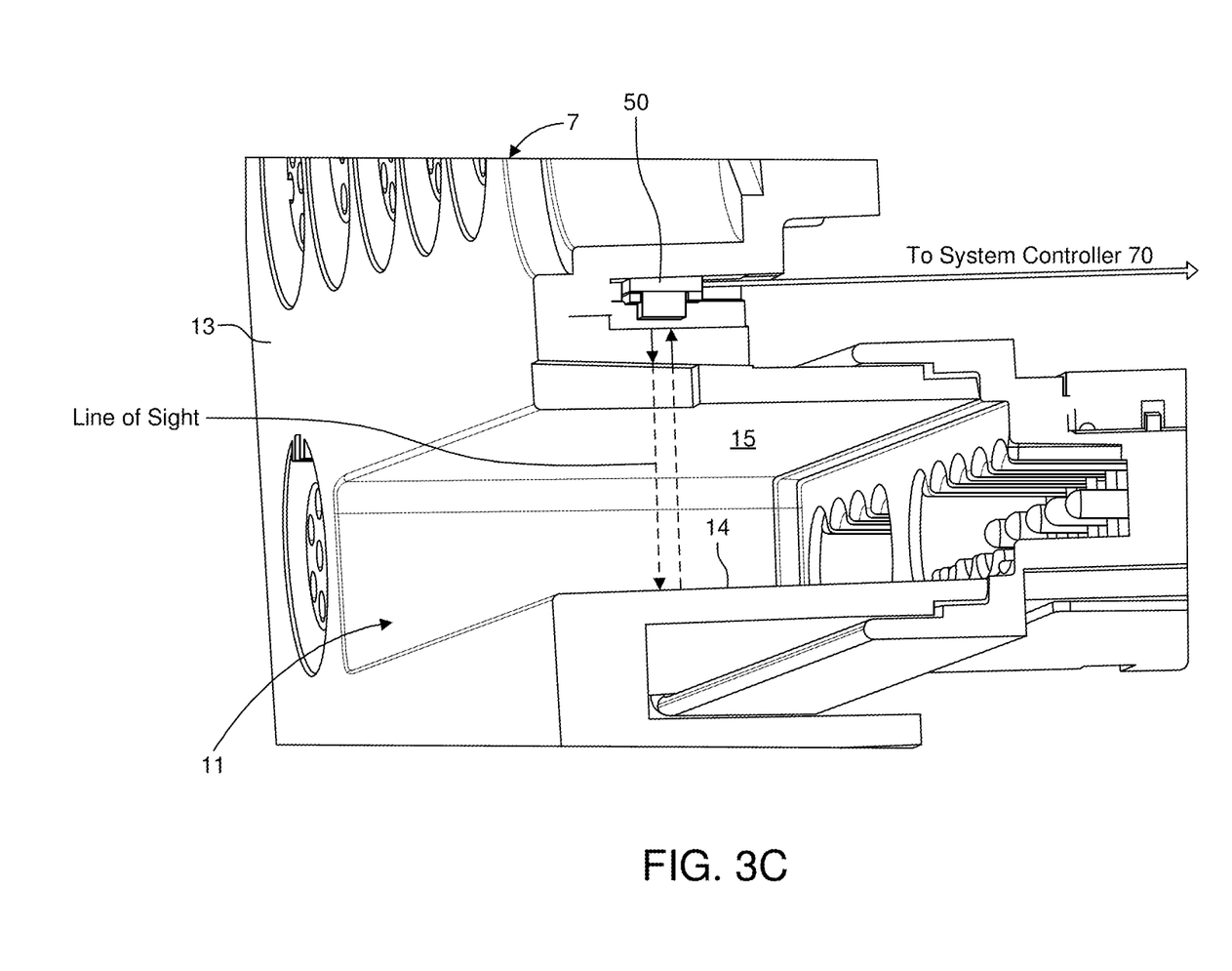

FIGS. 3A-3C illustrate a connector detection system according to one or more examples. In particular, the connector detection system may be provided at the patient monitoring device 7 and includes at least two cable detection sensors that are used to detect legacy or non-smart (e.g., non-EEPROM) cables. It is noted that, in examples in which a smart cable is connected, then the cable detection sensor that corresponds to the connector port at which the smart cable is received may be bypassed or ignored by a system controller 70. Thus, the cable detection methods may be directed to the detection of legacy cables that do not have circuitry that enables the patient monitoring device 7 to detect the presence thereof. In various embodiments, the system controller 70 is incorporated into patient monitoring device 7 and may be, for example, a processor, an FPGA, an ASIC, a DSP, a microcontroller, or similar processing device. The system controller 70 may include a memory, which may be, for example, a RAM, a memory buffer, a hard drive, a database, an EPROM, an EEPROM, a ROM, a flash memory, a hard disk, or any other non-transitory computer readable medium.

A first sensor 50 may be configured to detect a presence of an ECG lead set or ECG extension cable inserted at the ECG cable interface 11 and a second sensor 60 may be configured to detect a presence of an NIBP cable inserted at the NIBP cable interface 12. Both the first sensor 50 and the second sensor 60 may be optical sensors (e.g., bi-directional phototransceivers). Thus, they may be configured to transmit one or more light beams (e.g., infrared light beams) and detect a reflection thereof, where a transmitted light beam is reflected back by an object arranged within the transmission path of the transmitted light beams. A transmitted light beam may be a continuous light beam that is constantly output or may be one of a series of light pulses that are sequentially transmitted according to a predetermined frequency.

Both sensors 50 and 60 may include a photo receiver (e.g., a photodiode) and processing circuitry. The photo receiver may be configured to generate an electrical signal based on the received light and provide the electrical signal to the processing circuitry. The processing circuitry may be configured to detect a presence of an inserted cable based on the electrical signal and output a detection result to the system controller 70. In response to receiving an indication from an optical sensor that a cable has been inserted at the patient monitoring device 7, the system controller 70 may be configured to activate the frontend circuitry of the patient monitoring device 7 that corresponds to the connected cable type (e.g., ECG frontend circuitry 71 or NIBP frontend circuitry 72) by way of a control signal. The activated frontend circuitry is then enabled for receiving and processing measurements. For example, the ECG frontend circuitry 71 is enabled to receive and process ECG measurements from the ECG lead set 20 and the NIBP frontend circuitry 72 is enabled to receive and process NIBP measurements from the NIBP cable 40.

If the system controller 70 detects that the ECG lead set 20 has been connected to the patient monitoring device 7, the system controller 70 may also control the display 4 to display a menu and/or one or more prompts that request a user to input additional information related to ECG lead set 20. For example, the system controller 70 may request a user to provide a number of leads pertaining to the ECG lead set 20. The user input circuitry may provide the number of leads information to the system controller 70, which may subsequently provide the number of leads information or configuration information to the ECG frontend circuitry 71. Configuration settings within the ECG frontend circuitry 71 are then set for the processing and the displaying ECG data according to the number of leads indicated by the user.

The cable detection may also work in reverse. In the event that sensor 50 or sensor 60 no longer detects the presence of a respective cable, the sensor may indicate to the system controller 70 that the cable is no longer present, for example, due to disconnect and removal. In response to receiving an indication that a cable is no longer present, the system controller 70 may disable the corresponding frontend circuitry of the patient monitoring device 7 by way of a control signal in order to save power and processing resources.

As shown in FIGS. 3A-3C, the ECG cable interface 11 may be a connector port that has an interior volume 15 defined by one or more sidewalls. The optical sensor 50 may be arranged proximate to one side of the ECG cable interface 11 such that light beams are transmitted across the entire interior volume when the connector 21 or connector 31 is not present. Light beams that impinge upon the distant sidewall 14 located across the interior volume from the optical sensor 50 may be absorbed by the distant sidewall 14 and/or may be at least partially reflected back at the optical sensor 50 via backscattering.

In contrast, when the connector 21 or connector 31 is present by insertion into the interior volume 15, the connector 21 or connector 31 may be inserted into the line of sight of the optical sensor 50 (i.e., into the transmission path of the transmitted light). The connector 21, 31 blocks the transmitted light and reflects the light back at the optical sensor 50. The processing circuitry of the optical sensor 50 may be configured to distinguish between whether a connector is present within the interior volume 15 based on either a signal strength comparison (e.g., via amplitude analysis) or by a direct time-of-flight comparison (e.g., via timing analysis).

For example, the signal strength of light reflected by either connector 21 or connector 31 should be higher than the signal strength of light reflected by the distant sidewall 14 when a connector is not present. Thus, the processing circuitry of the optical sensor 50 may compare a measured amplitude of a sensor signal to a predetermined reference threshold (e.g., a baseline). If the measured amplitude is greater than the predetermined reference threshold, the optical sensor 50 may determine that a connector is present and outputs an indication to the system controller 70. On the other hand, if the measured amplitude is equal to or less than the predetermined reference threshold, the optical sensor 50 determines that a connector is not present and outputs an indication to the system controller 70. Such a comparison can be performed using a comparator (e.g., a 1-bit analog-to-digital converter (ADC)) that generates a "1" if a connector is present and a "0" is a connector is not present, or vice versa. Amplitude analysis may also filter out ambient light by setting the predetermined reference threshold high enough so as not to trigger a false detection.

Similarly, if time-of-flight is used, the time-of-flight for a light signal to travel from the optical sensor 50 and back (via reflection) should be longer if a connector is not present and should be shorter if a connector is present. Thus, the processing circuitry of the optical sensor 50 may compare a measured time-of-flight to a predetermined reference threshold. If the measured time-of-flight is less than the predetermined reference threshold, the optical sensor 50 determines that a connector is present and outputs an indication to the system controller 70. On the other hand, if the measured time-of-flight is equal to or greater than the predetermined reference threshold, the optical sensor 50 may determine that a connector is not present and outputs an indication to the system controller 70. Such a comparison may be performed using a comparator (e.g., a 1-bit ADC) that generates a "1" if a connector is present and a "0" is a connector is not present, or vice versa.

It can be appreciated that the optical sensor 50 may be disposed in any location that results in the light beams being backscattered by the connector 21 or connector 31 when the respective connector is present, and not being backscattered by the connector 21 or connector 31 when the respective connector is not present.

A similar concept may be used for detecting the presence of an NIBP cable. As shown in FIGS. 3A-3C, the NIBP cable interface 12 may be a connector port having an interior volume 18 defined by one or more sidewalls. The optical sensor 60 may be arranged proximate to one end of the NIBP cable interface 12 and may be configured to transmit light beams outward across the interior volume 18 into free space. In other words, the light beams are transmitted in a direction that exits the interior volume 18. Typically, this means that there are no reflected light beams unless connector 41 is present within the line of sight.

The connector 41 may include a cuff fitting 42 that extends outward in a radial direction from the center of the connector 41. When the connector 41 is inserted into the interior volume 18, the cuff fitting 42 is arranged in the line of sight of optical sensor 60. As such, transmitted light is reflected back at the optical sensor 60 by the cuff fitting 42 where it can be detected and analyzed. The processing circuitry of the optical sensor 60 may be configured to distinguish between whether a connector is present within the interior volume 18 and connected to the patient monitoring device 7 based on either a signal strength comparison (e.g., via amplitude analysis) or by a direct time-of-flight comparison (e.g., via timing analysis).

The connector detection system may further include an EEPROM detector 80 (i.e., a smart cable detector) that is configured to detect when a smart ECG cable (i.e., a smart ECG lead set) is connected to the ECG cable interface 11. In the event that a smart ECG cable is connected to the ECG cable interface 11, the EEPROM detector 80 may transmit an EEPROM detection signal to the system controller 70. In response to the EEPROM detection signal, the system controller 70 may disregard the output signal received from the optical sensor 50 and may also activate the ECG frontend circuitry 71. The EEPROM detector 80 may also receive ECG lead set information, such as a number of leads, and provide the ECG lead set information to the system controller 70. The system controller 70 may configure settings at the ECG frontend circuitry 71 based on the number of leads.

Figure 4:
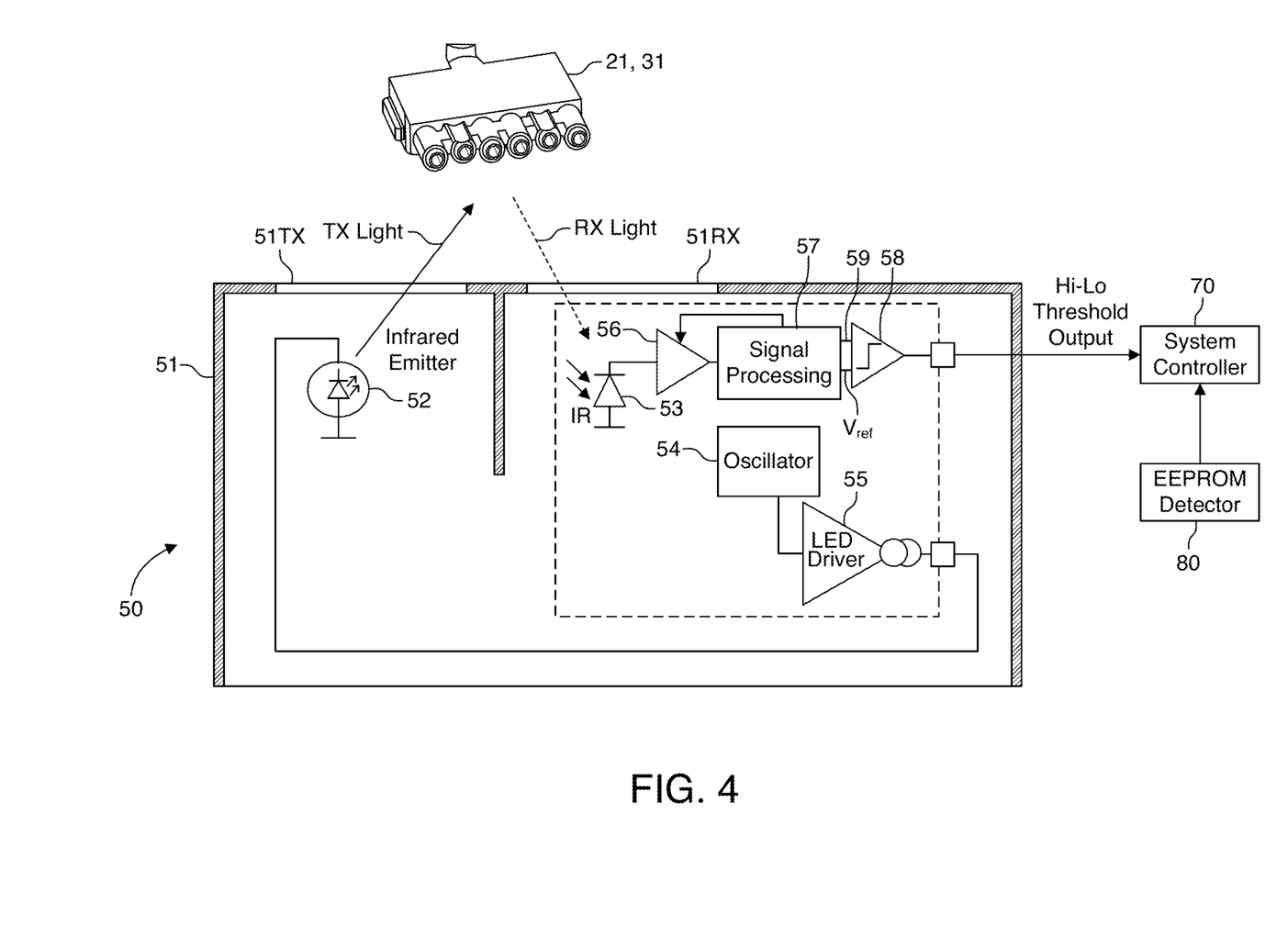
FIG. 4 shows a schematic block diagram of an optical sensor according to one or more embodiments.

FIG. 4 shows a schematic block diagram of an optical sensor according to one or more embodiments. The optical sensor is shown as optical sensor 50. However, the optical sensor as shown in FIG. 4 may also be used as optical sensor 60.

The optical sensor 50 may include a housing 51 that comprises a transmitter window 51TX and a receiver window 51RX. The transmitter window 51TX may be transparent and permit the transmission of light beams (TX light) out from the housing 51, along the line of sight. Similarly, the receiver window 51 RX is transparent and permits the transmission of reflected light beams (RX light) into the housing.

The optical sensor 50 may further include an emitter 52 that transmits light beams and a receiver 53 that detects light. In some embodiments, the emitter 52 and receiver 53 may be combined as a single component, such as a bi-directional diode that can both transmit and detect light. The emitter 52 may be driven by an oscillator 54 and a light emitting diode (LED) driver 55. The oscillator 54 may define a pulse frequency and the LED driver 55 may transmit trigger signals to the emitter 52 in accordance with the pulse frequency. The emitter 52, in turn, may transmit light pulses in accordance with the trigger signals.

The receiver 53 may generate electrical signals based on received light. The amplitudes of the electrical signals may be proportional to the intensity or signal strength of the received light, with light being reflected back by connector 21 or connector 31 having the highest intensity. The electrical signals may also be used to stop a counter that is used to calculate a time-of-flight of a light pulse.

The processing circuitry of the optical sensor 50 may include an amplifier 56, a signal processor 57, and a comparator 58. The amplifier 56 may amplify the electrical signals generated by the receiver 53 such that they can be processed. The signal processor 57 may also set the gain of the amplifier 56.

The signal processor 57 may perform signal conditioning on the amplified electrical signals so that they are suitable for use by the comparator 58. The signal processor 57 may also set the predetermined reference threshold Vref used by the comparator 58 for performing its comparison. The signal processor 57 may output a measurement signal 59 (e.g., a voltage signal) that either represents the measured amplitude of the electrical signal generated by the receiver 53 or the measured time-of-flight.

The comparator 58 may be configured to generate a connector detection signal based on the predetermined reference threshold Vref and whether an amplitude analysis or time-of-fight analysis is being used. The output of the comparator 58 may be transmitted to the system controller 70 and the system controller 70 determines whether a connector is present and performs further actions described above based on the result.

In view of the above, the patient monitoring device 7, by way of sensors 50 and 60, provides seamless workflow for the use of mixed accessories that include smart cables and legacy cables. Accordingly, the patient monitoring device 7 may be configured to detect when legacy cables, connectors, lead sets, and the like have been plugged in and activate the corresponding frontend circuitry as well as prompt the use for additional information when relevant.

While various embodiments have been disclosed, it will be apparent to those skilled in the art having the benefit of this disclosure that various changes and modifications can be made which will achieve some of the advantages of the concepts disclosed herein without departing from the spirit and scope of the invention. It will also be apparent to those skilled in the art having the benefit of this disclosure that other components performing the same functions may be suitably substituted. It is to be understood that other embodiments may be utilized and structural or logical changes may be made without departing from the scope of the present invention. It should be mentioned that features explained with reference to a specific figure may be combined with features of other figures, even in those not explicitly mentioned. Such modifications to the general inventive concept are intended to be covered by the appended claims and their legal equivalents.

Furthermore, the following claims are hereby incorporated into the detailed description, where each claim may stand on its own as a separate example embodiment. While each claim may stand on its own as a separate example embodiment, it is to be noted that—although a dependent claim may refer in the claims to a specific combination with one or more other claims—other example embodiments may also include a combination of the dependent claim with the subject matter of each other dependent or independent claim. Such combinations are proposed herein unless it is stated that a specific combination is not intended. Furthermore, it is intended to include also features of a claim to any other independent claim even if this claim is not directly made dependent to the independent claim.

It is further to be noted that methods disclosed in the specification or in the claims may be implemented by a device having means for performing each of the respective acts of these methods. For example, the techniques described in this disclosure may be implemented, at least in part, in hardware, software, firmware, or any combination thereof. For example, various aspects of the described techniques may be implemented within one or more processors, including one or more microprocessors, DSPs, ASICs, or any other equivalent integrated or discrete logic circuitry, as well as any combinations of such components.

Further, it is to be understood that the disclosure of multiple acts or functions disclosed in the specification or in the claims may not be construed as to be within the specific order. Therefore, the disclosure of multiple acts or functions will not limit these to a particular order unless such acts or functions are not interchangeable for technical reasons. Furthermore, in some embodiments a single act may include or may be broken into multiple sub acts. Such sub acts may be included and part of the disclosure of this single act unless explicitly excluded.

What is claimed is:

1. A connector detection system, comprising:
   a connector interface comprising a connector port having an interior volume configured to receive a connector of a cable; and
   an optical sensor comprising:
      a transmitter configured to transmit a light beam across the interior volume;
      a receiver configured to monitor for a reflected light beam corresponding to the transmitted light beam; and
      processing circuitry configured to determine whether the connector is inserted into the interior volume based on a monitoring for the reflected light beam; wherein:
      the processing circuitry comprises a comparator configured to compare a signal amplitude to a predetermined reference threshold, the signal amplitude being derived from the electrical signal and corresponding to an intensity of the received reflected light beam.

2. The connector detection system of claim 1, wherein:
   the receiver is configured to generate an electrical signal in response to receiving the reflected light beam, and
   the processing circuitry is configured to determine whether a connector is inserted into the interior volume based on the electrical signal.

3. The connector detection system of claim 2, wherein:
   the processing circuitry determines a time-of-flight based on the electrical signal, converts the determined time-of-flight to a signal value, and compares the signal value to a predetermined reference threshold,
   the processing circuitry includes a comparator,
   the comparator generates a first output value on a first condition that the signal value is greater than the predetermined reference threshold, thereby indicating that the connector is inserted into the interior volume, and
   the comparator generates a second output value on a second condition that the signal value is less than the predetermined reference threshold, thereby indicating that the connector is not inserted into the interior volume.

4. The connector detection system of claim 2, wherein:
   the cable port comprises a distant sidewall that defines part of the interior volume,
   the distant sidewall is located across the interior volume opposite to the optical sensor,
   the distant sidewall causes the transmitted light beam to be reflected back to the receiver as the reflected light beam in the absence of the connector within the interior volume, and
   the connector causes the transmitted light beam to be reflected back to the receiver as the reflected light beam in the presence of the connector within the interior volume.

5. The connector detection system of claim 2, wherein:
   the comparator is configured to generate a first output value upon determining that the signal amplitude is greater than the predetermined reference threshold, thereby indicating that the connector is inserted into the interior volume, and
   the comparator is configured to generate a second output value upon determining that the signal amplitude is less than the predetermined reference threshold, thereby indicating that the connector is not inserted into the interior volume.

6. The connector detection system of claim 5, further comprising:
   a system controller is configured to receive an output of the comparator,
   wherein the system controller is configured to activate frontend circuitry to process measurement signals received from the connector in response to receiving the first output value, and
   wherein the system controller is configured to disable the frontend circuitry in response to receiving the second output value.

7. The connector detection system of claim 5, further comprising:
   a display; and
   a system controller configured to receive an output of the comparator,
   wherein the system controller is configured to control the display to display at least one prompt to a user to input cable information corresponding to the cable in response to receiving the first output value.

8. The connector detection system of claim 7, wherein:
   the connector interface is an electrocardiogram (ECG) interface and the cable is an ECG lead set, and
   the connector information is a number of leads of the ECG lead set.

9. The connector detection system of claim 1, wherein:
   the receiver is configured to generate an electrical signal in response to receiving the reflected light beam, and
   the processing circuitry is configured to determine that the connector is inserted into the interior volume in response to receiving the electrical signal and to determine that the connector is not inserted into the interior volume in the absence of the electrical signal.

10. The connector detection system of claim 9, wherein the processing circuitry is configured to determine that the connector is fully inserted into the interior volume based on an amplitude of the electrical signal.

11. The connector detection system of claim 9, wherein:
    the processing circuitry is configured to determine whether received light is the reflected light beam,
    the processing circuitry comprises a comparator configured to compare a signal amplitude to a predetermined reference threshold, the signal amplitude being derived from the receiver and which corresponds to an intensity of the received light, the comparator is configured to generate a first output value on a first condition that the signal amplitude is greater than the predetermined reference threshold, thereby indicating that the received light is the reflected light beam, and the comparator is configured to generate a second output value on a second condition that the signal amplitude is less than the predetermined reference threshold, thereby indicating that the received light is not the reflected light beam.

12. The connector detection system of claim 9, wherein:
the transmitter is configured to transmit the light beam across the interior volume into free space in the absence of the connector within the interior volume, and the connector causes the transmitted light beam to be reflected back to the receiver as the reflected light beam in the presence of the connector within the interior volume.

13. The connector detection system of claim 9, wherein the connector interface is a non-invasive blood pressure (NIBP) interface and the cable is an NIBP cable.

14. The connector detection system of claim 9, further comprising:
a system controller configured to receive an output of a comparator of the processing circuitry, wherein the system controller is configured to activate frontend circuitry configured to process measurement signals received from the connector in response to receiving the first output value, and wherein the system controller is configured to disable the frontend circuitry in response to receiving the second output value.

15. A patient monitoring device, comprising:
frontend circuitry configured to receive and process physiological measurements received from a cable connected to a patient;

a connector interface comprising a connector port having an interior volume configured receive a connector of the cable;

an optical sensor comprising:
a transmitter configured to transmit a light beam across the interior volume;

a receiver configured to monitor for a reflected light beam corresponding to the transmitted light beam; and processing circuitry configured to determine whether a connector is inserted into the interior volume based on a monitoring for the reflected light beam; and a system controller configured to activate the frontend circuitry in response to the processing circuitry determining that the connector is inserted into the interior volume and deactivate the frontend circuitry in response to the processing circuitry determining that the connector is not inserted into the interior volume.

16. The patient monitoring device of claim 15, wherein:
the receiver is configured to generate an electrical signal in response to receiving the reflected light beam, and the processing circuitry is configured to determine whether the connector is inserted into the interior volume based on the electrical signal.

17. The patient monitoring device of claim 15, wherein:
the receiver is configured to generate an electrical signal in response to receiving the reflected light beam, and the processing circuitry is configured to determine that the connector is inserted into the interior volume in response to receiving the electrical signal and determine that the connector is not inserted into the interior volume in the absence of the electrical signal.

18. The patient monitoring device of claim 15, wherein the connector interface is a non-invasive blood pressure (NIBP) interface and the cable is an NIBP cable.

19. The patient monitoring device of claim 15, further comprising:
a display, wherein the system controller is configured to receive an output of the processing circuitry indicating whether the connector is inserted into the interior volume, and control the display to display at least one menu icon prompting a user to input cable information corresponding to the cable in response to receiving an indication that the connector is inserted into the interior volume.

20. The patient monitoring device of claim 19, wherein:
the connector interface is an electrocardiogram (ECG) interface and the cable is an ECG lead set, and the connector information is a number of leads of the ECG lead set.

\* \* \* \* \*